United States Patent [19]
Clode et al.

[11] Patent Number: 5,750,007
[45] Date of Patent: May 12, 1998

[54] PROCESS FOR THE RECOVERY OF A CARBONYLATION PRODUCT

[75] Inventors: Kirsten Everald Clode, North Humberside; Derrick John Watson, East Yorkshire, both of England; Carl Josef Elsa Vercauteren, St Gillis-Waas, Belgium

[73] Assignee: BP Chemicals Limited, London, England

[21] Appl. No.: 454,620

[22] Filed: May 31, 1995

Related U.S. Application Data

[63] Continuation of Ser. No. 173,694, Dec. 23, 1993, abandoned.

[30] Foreign Application Priority Data

Mar. 26, 1993 [GB] United Kingdom ............ 9306409

[51] Int. Cl.$^6$ ............ B01D 3/42; C07C 51/12; C07C 51/44
[52] U.S. Cl. ............ 203/3; 203/14; 203/29; 203/73; 203/80; 203/88; 159/2.1; 560/232; 562/519; 502/325
[58] Field of Search ............ 203/73, 3, 79, 203/14, 88, 1, 80, 29, 92, 95, DIG. 21; 562/519, 517, 520; 560/232; 159/2.1; 502/325, 500

[56] References Cited

U.S. PATENT DOCUMENTS

| | | |
|---|---|---|
| 3,772,380 | 11/1973 | Paulik et al. . |
| 4,008,131 | 2/1977 | Price ............ 203/98 |
| 4,102,922 | 7/1978 | Price . |
| 4,549,937 | 10/1985 | Erpenbach et al. ............ 203/40 |
| 4,946,029 | 8/1990 | Frank et al. ............ 203/91 |
| 4,994,608 | 2/1991 | Torrence et al. ............ 203/88 |
| 5,026,908 | 6/1991 | Smith et al. ............ 203/88 |
| 5,227,520 | 7/1993 | Cooper et al. ............ 203/71 |
| 5,374,774 | 12/1994 | Ochiai ............ 562/519 |
| 5,416,237 | 5/1995 | Aubigne et al. ............ 562/519 |
| 5,599,976 | 2/1997 | Scates et al. ............ 562/519 |

FOREIGN PATENT DOCUMENTS

| | | |
|---|---|---|
| 837644 | 3/1970 | Canada . |
| 384652 | 8/1929 | European Pat. Off. . |
| 0135286 | 3/1985 | European Pat. Off. . |
| 0441260 | 8/1991 | European Pat. Off. . |
| 0506240 | 9/1992 | European Pat. Off. . |
| 0573189 | 12/1993 | European Pat. Off. . |
| 1767150 | 5/1972 | Germany . |
| 62-145041 | 6/1987 | Japan . |
| 1233121 | 5/1971 | United Kingdom . |
| 1234641 | 6/1971 | United Kingdom . |
| 1234642 | 6/1971 | United Kingdom . |
| 1355146 | 5/1974 | United Kingdom . |
| 1355146 | 6/1974 | United Kingdom . |
| 203385 | 5/1990 | United Kingdom . |

OTHER PUBLICATIONS

Forster, J. Chem. Soc., Dalta Trans. 1979, pp. 1639–1645.
Luft et al, J. Mol. Cat., (1983), 20, 175–184.
Schrod, J. Mol. Cat., (1983), 22, 169–173.
Monti, et al, Organometallics, (1991), 10, 4015–4020.
Crabtree et al, Inorg. Chem., (1982), 21, 1273–1275.

*Primary Examiner*—Virginia Manoharan
*Attorney, Agent, or Firm*—Brooks Haidt Haffner & Delahunty

[57] ABSTRACT

A process for the recovery of a carbonylation product from a liquid reaction composition of an iridium-catalysed carbonylation reaction of a carbonylatable reactant includes subjecting the composition to a vaporization with or without the addition of heat to produce a vapor-fraction and a liquid fraction, the vapor fraction includes carbonylation product and the liquid fraction has a water concentration of at least 0.5% by weight to stabilise the iridium catalyst.

3 Claims, 3 Drawing Sheets

PROCESS FOR THE RECOVERY OF A CARBONYLATION PRODUCT

This application is a continuation of application Ser. No. 08/173,694, filed Dec. 23, 1993, now abandoned.

The present invention relates to a process for the recovery of a carbonylation product from a liquid carbonylation reaction composition and in particular to a process for the recovery of a carbonylation product from a liquid carbonylation reaction composition comprising free or combined iridium carbonylation catalyst.

British patent GB 1,234,641 describes a process for the production of an organic acid or an ester by carbonylation of an alcohol, halide, ester, ether or phenol in the presence of a noble metal catalyst selected from iridium, platinum, palladium, osmium and ruthenium and their compounds and a promoter which is halogen or halogen compound. In the liquid-phase embodiment illustrated in FIG. 1 in GB 1,234, 641 the liquid effluent from the reactor has its pressure let down and is then introduced into a distillation or flash column 30 where the lower boiling compounds consisting principally of methyl acetate, methyl iodide and unreacted methanol are separated from acetic acid and the other less volatile components such as the catalyst system. The lower boiling components are recycled to the reactor. The acetic acid and other higher boiling compounds are removed from column 30 and enter distillation or flash column 40. In this column acetic acid which may contain water is separated from the other high boiling components, principally comprised of the catalyst. The acetic acid is withdrawn and may be further purified to remove water. The high boiling components are recycled to the reactor. If no component higher boiling than acetic acid, such as a high boiling solvent, is present, then some acetic acid may be recycled to return the catalyst to the reactor.

A similar reaction scheme is described in related U.S. Pat. No. 3,772,380 which relates to a process for the preparation of carboxylic acids and esters by carbonylation of alcohols and their ester, ether and halide derivatives in the presence of an iridium/halogen catalyst system.

According to British patent GB 1,355,146 conventional processing schemes involving distillation for the separation of carbonylation products from the liquid reaction mass pose problems of catalyst inactivation and precipitation for rhodium and iridium carbonylation catalyst systems such as those described in GB 1,234,461 because these tend to decompose and become inactive when they come in to contact with the hot surfaces in distillation column reboilers. One solution proposed in GB 1,355,146 is to utilise extremely large distillation column reboilers. Another solution proposed in GB 1,355,146 is to pass at least a portion of the liquid reaction mass to a separation zone maintained at a pressure substantially below that of the reaction zone thus vaporising at least a portion of the carbonylation products without the addition of heat. In a preferred process the liquid remaining in the separation zone after vaporisation of at least a portion of the carbonylation products is re-cycled to the reaction zone. The examples given only relate to the use of rhodium catalysts and there are no details given of what components are present in the unvaporised liquid fraction when iridium carbonylation catalysts are used.

The technical problem to be solved by the present invention is to provide a process for the recovery of a carbonylation product from a liquid carbonylation reaction composition comprising free or combined iridium carbonylation catalyst in which the catalyst has reduced tendancy to lose its stability and/or solubility.

Thus, according to the present invention there is provided a process for the recovery of a carbonylation product from a liquid reaction composition of an iridium-catalysed carbonylation reaction of a carbonylatable reactant, which liquid composition comprises carbonylation product and free or combined iridium carbonylation catalyst, which process comprises subjecting the liquid carbonylation reaction composition to a vaporisation, with or without the addition of heat, to produce a vapor fraction comprising carbonylation product and a liquid fraction comprising iridium carbonylation catalyst and separating the liquid and vapor fractions, and in which process there is maintained in the liquid fraction a concentration of water of at least 0.5% by weight.

The present invention solves the technical problem presented above by the use of water to stabilise the iridium catalyst during the recovery process.

In the process of the present invention, the vaporisation may be performed as a flash vaporisation with or without the addition of heat. In an adiabatic flash the pressure of the composition at elevated temperature is reduced without the addition of heat. In an isothermal flash the pressure of the composition at elevated temperature is reduced and the temperature of the composition is maintained by the addition of heat. Either of these types of flash vaporisations may be used or a combination of both, for example addition of only some heat and reducing pressure or addition of heat without a change in pressure.

Thus, for example, in one embodiment using an adiabatic flash, the liquid carbonylation reaction composition at elevated temperature and pressure such as, for example, that required for the carbonylation reaction, is introduced into a flash zone which is at a substantially lower pressure than the elevated pressure of the carbonylation reaction composition. This causes at least a portion of the liquid carbonylation reaction composition to vaporise and produce the vapor and liquid fractions, which may be removed separately from the flash zone. A suitable adiabatic flash may be performed by, for example, introducing liquid carbonylation reaction composition having a temperature of about 100° to 250° C. and a pressure of about 10 to 100 barg into a flash zone maintained at a temperature of about 80° to 200° C. and a pressure of about 0 to 20 barg.

The vaporisation may also be performed by the addition of heat to the liquid carbonylation reaction composition to vaporise at least a portion of the composition and produce the vapor and liquid fractions. This may be an isothermal flash wherein the temperature of the composition is maintained by the addition of heat. A suitable isothermal flash vaporisation may be performed at a temperature of 80° to 200° C. and a pressure of 0 to 20 barg.

The vaporisation may be performed in a short residence vaporiser wherein heat is supplied to the liquid carbonylation reaction composition to vaporise a portion thereof whether or not the pressure is reduced.

The vaporisation may also be performed in a fractional distillation zone. In this embodiment, liquid carbonylation reaction composition is introduced into a distillation zone, the liquid fraction comprising iridium carbonylation catalyst is removed from the base of the distillation zone. The vapor fraction comprising carbonylation product passes up the distillation zone and may be removed either as a liquid or vapor at any point above the base of the distillation zone.

More than one vaporisation stage may be used in the process of the present invention provided that in each stage the concentration of water present in the liquid fraction is sufficient to maintain the stability and solubility of the iridium carbonylation catalyst. Thus, two or more flash vaporisations may be used in sequence each independently with or without the addition of heat. Alternatively, one or more flash vaporisations may precede a fractional distillation zone.

When heat is added to effect the vaporisation a suitable source of heat is steam heating.

The residence time of the liquid fraction in the vaporisation zone or distillation zone is preferably relatively short, for example a liquid fraction residence time of 1 to 60 minutes.

Whatever the design of the equipment used for the vaporisation, the water concentration in the liquid fraction comprising the iridium carbonylation catalyst is at least 0.5% by weight, preferably about 0.5 to 50% by weight, more preferably 1 to 10% by weight. The water may be introduced to the vaporisation as a component in the liquid carbonylation reaction composition and/or may be introduced separately to the vaporisation.

The free or combined iridium carbonylation catalyst concentration in the liquid fraction may suitably be in the range from 0.01% by weight iridium up to the limit of solubility of the catalyst in the liquid fraction, preferably 0.05 to 2.0% by weight.

Preferably, the liquid fraction also comprises halide carbonylation promoter, for example an alkyl halide, preferably an iodide promoter and most preferably methyl iodide. Suitably the halide promoter is present at a concentration of 0.01 to 20% by weight.

Preferably, the liquid fraction also comprises ester derivative of the carbonylatable reactants, for example methyl acetate. Suitably the ester derivative is present at a concentration of 1 to 50% by weight.

The preferred and most preferred concentrations of these components in the liquid fraction are independently set out in Table 1 below.

TABLE 1

| CONCENTRATIONS OF COMPONENTS IN LIQUID FRACTION | | |
|---|---|---|
| COMPONENT | PREFERRED % BY WEIGHT | MOST PREFERRED % BY WEIGHT |
| Water | 0.5–50 | 1.0–15 |
| Iridium catalyst | 0.05–2.0 | 0.1–1.0 |
| Halide promoter | 0.01–20 | 0.1–10 |
| Ester derivative | 2–50 | 3–35 |

The liquid carbonylation reaction composition of any suitable liquid-phase, iridium-catalysed carbonylation process of carbonylatable reactants may be used in the process of the present invention.

Thus, a suitable carbonylation process may comprise a liquid phase, iridium-catalysed carbonylation of an alcohol, ester, hydrocarbyl halide and/or hydrocarbyl ether reactant to produce a corresponding carboxylic acid and/or carboxylic acid ester. In such a process carbon monoxide is contacted with a liquid carbonylation reaction composition comprising carbonylatable reactant and/or an ester derivative thereof, iridium carbonylation catalyst, halide carbonylation promoter and preferably, a finite concentration of water.

A suitable alcohol carbonylatable reactant is any alcohol having from 1 to 20 carbon atoms and at least one hydroxyl group. Preferably, the alcohol is a monofunctional aliphatic alcohol having from 1 to 8 carbon atoms. Most preferably, the alcohol is methanol, ethanol and/or propanol. A mixture comprising more than one alcohol may be used. The carbonylation product of the alcohol will be a carboxylic acid having one carbon atom more than the alcohol and/or an ester thereof with the alcohol reactant. A particularly preferred reactant is methanol, the carboxylic acid product of which is acetic acid and/or methyl acetate.

A suitable ester carbonylatable reactant is any ester of an alcohol and a carboxylic acid. Preferably the ester reactant is an ester of a carboxylic acid and an alcohol which alcohol has from 1 to 20 carbon atoms. More preferably the ester reactant is an ester of a carboxylic acid and a monofunctional aliphatic alcohol which alcohol has from 1 to 8 carbon atoms. Most preferably the ester reactant is an ester of a carboxylic acid and methanol, ethanol or propanol. Preferably the ester reactant is an ester of an alcohol and the carboxylic acid product. Preferably the ester reactant has up to 20 carbon atoms. A mixture of ester reactants may be used. The carboxylic acid carbonylation product of the ester reactant will be a carboxylic acid having one carbon atom more than the alcohol component of the ester reactant. A particularly preferred ester reactant is methyl acetate, the carboxylic acid carbonylation product of which is acetic acid.

A suitable halide carbonylatable reactant is any hydrocarbyl halide having up to 20 carbon atoms. Preferably the halide reactant is an iodide or a bromide. More preferably the halide component of the hydrocarbyl halide reactant is the same halide as that of the halide carbonylation promoter. Most preferably the hydrocarbyl halide is a hydrocarbyl iodide, most preferably methyl iodide, ethyl iodide or propyl iodide. A mixture of hydrocarbyl halide reactants may be used. The carboxylic acid product of the hydrocarbyl halide reactant will be a carboxylic acid having one more carbon atom than the hydrocarbyl halide reactant. The ester carbonylation product of the hydrocarbyl halide will be the ester of the hydrocarbyl halide and a carboxylic acid having one more carbon atom than the hydrocarbyl halide.

A suitable ether carbonylatable reactant is any hydrocarbyl ether having up to 20 carbon atoms. Preferably the ether reactant is a dialkyl ether, most preferably dimethyl ether, diethyl ether or dipropyl ether. A mixture of ethers may be used. The carbonylation products of the ether reactant will be carboxylic acids having one carbon atom more than each of the hydrocarbyl groups of the ether and/or esters derivatives thereof. A particularly preferred ether carbonylation reactant is dimethyl ether, the carboxylic acid product of which is acetic acid.

A mixture of alcohol, ester, halide and ether carbonylatable reactants may be used in the carbonylation process. More than one alcohol, ester, halide and/or ether may be used. A particularly preferred carbonylatable reactant is methanol and/or methyl acetate, the carboxylic acid carbonylation products of which are acetic acid.

The iridium carbonylation catalyst in the liquid carbonylation reaction composition may comprise any iridium-containing compound which is soluble in the liquid reaction composition. It may be added to the liquid carbonylation reaction composition for the carbonylation reaction in any suitable form which dissolves in the liquid reaction composition or is convertable to a soluble form. Examples of suitable iridium-containing compounds which may be used include $IrCl_3$, $IrI_3$, $IrBr_3$, $Ir(CO)_2I_2$, $Ir(CO)_2Cl_2$, $Ir(CO)_2Br_2$, $IrCl_3.4H_2O$, $IrBr_3.4H_2O$, $Ir_2(CO)_8$, iridium metal, iridium acetate, $Ir_2O_3$, $IrO_2$, $Ir(acac)(CO)_2$ and $Ir(acac)_2$. Preferably, the iridium catalyst concentration in the liquid carbonylation reaction composition is in the range 50 to 10000 ppm by weight of iridium, more preferably 100 to 6000 ppm by weight of iridium.

The halide carbonylation promoter for the suitable carbonylation reaction may be an iodide or bromide compound preferably an iodide. Preferably, the halide promoter is the halide derivative of the carbonylatable reactant, that is a hydrocarbyl halide. Most preferably, the halide carbonylation promoter is methyl iodide. Preferably the concentration of halide carbonylation promoter in the liquid carbonylation reaction composition is in the range 1 to 20% by weight, more preferably 1 to 10% by weight.

The carbon monoxide feed to the suitable carbonylation reaction may be essentially pure or may contain inert impurities such as carbon dioxide, methane, nitrogen, noble gases, water and $C_1$ to $C_4$ paraffinic hydrocarbons. Hydrogen may be present in the suitable carbonylation reactor. Hydrogen may be generated in situ or fed to the carbonylation reactor with the carbon monoxide and/or separately therefrom. The partial pressure of carbon monoxide in the suitable carbonylation reaction may suitably be in the range 1 to 70 barg.

The pressure of the suitable carbonylation reaction is suitably in the range 10 to 100 barg. The temperature of the suitable carbonylation reaction is suitably in the range 100° to 250° C.

The liquid carbonylation reaction composition may also comprise ester derivative of the carbonylatable reactants preferably in the range 0.1 to 75% by weight, more preferably in the range 1.0 to 60% by weight.

The liquid carbonylation reaction composition may comprise water. The water may be formed in situ in the carbonylation reaction, for example by the esterification reaction between alcohol reactant and carboxylic acid product. The water may be introduced to the carbonylation reactor together with or separately from the other liquid reactants such as esters, for example methyl acetate. Water may be separated from reaction composition withdrawn from the reactor and recycled in controlled amounts to maintain the required concentration in the carbonylation reaction composition. The concentration of water in the liquid carbonylation reaction composition may be at least 0.1% by weight. Typically, and depending upon the other components of the liquid reaction composition, the water concentration in the liquid carbonylation reaction composition may be at least 0.1% by weight and up to 30% by weight preferably up to 15% by weight, most preferably the water concentration is about 2 to 8% by weight.

The components in the liquid carbonylation reaction composition which are more volatile than carbonylation product may be recovered from the carbonylation reaction composition in a preliminary recovery stage before the carbonylation product is recovered from the remaining carbonylation reaction composition. These more volatile components may be, for example, carbonylatable reactant and/or ester derivative thereof and carbonylation halide promoter. These volatile components may be recycled to the carbonylation reaction. A suitable preliminary recovery stage may comprise flash vaporisation with or without the addition of heat.

In particular, it has been found that in the liquid phase, iridium-catalysed carbonylation of an alcohol, ester, hydrocarbyl halide and/or hydrocarbyl ether reactant to produce carboxylic acid, the concentration of ester derivative of the reactant necessary in the liquid phase reaction composition to achieve a suitable rate of reaction is relatively high. This ester derivative may be recovered from the liquid carbonylation reaction composition in a preliminary vaporisation before the carbonylation product is recovered.

Thus, according to one embodiment of the present invention there is provided a process for the recovery of a carboxylic acid carbonylation product of an alcohol, ester, hydrocarbyl halide and/or hydrocarbyl ether carbonylatable reactant, from a liquid carbonylation reaction composition comprising carboxylic acid carbonylation product, free or combined iridium carbonylation catalyst and ester derivative of the carbonylatable reactant which process comprises (a) subjecting the liquid carbonylation reaction composition to a vaporisation in a first vaporisation zone to produce, with or without the addition of heat, a first vapor fraction comprising at least a portion of the ester derivative in the liquid carbonylation reaction composition and a first liquid fraction comprising the remainder of the ester derivative in the liquid carbonylation reaction composition, at least a portion of the carboxylic acid product and the iridium carbonylation catalyst, and maintaining a concentration of water of at least 0.5% by weight in the first liquid fraction and (b) passing the first liquid fraction to a second vaporisation zone wherein the first liquid fraction is subjected to a vaporisation, with or without the addition of heat, to produce a second vapor fraction comprising carboxylic acid carbonylation product and a second liquid fraction comprising iridium carbonylation catalyst and maintaining in the second liquid fraction a concentration of water of at least 0.5% by weight.

In this embodiment, the first vapor fraction and the second liquid fraction may be recycled to the carbonylation reaction. The second vapor fraction comprising carboxylic acid carbonylation product may be further purified by conventional means such as fractional distillation in one or more fractional distillation zones to recover carboxylic acid carbonylation product from the other components which may be recycled to the carbonylation reaction. Thus, for example, the second vapor fraction may be introduced into a distillation zone and subjected to fractional distillation in which a heads process stream comprising halide or halide compound carbonylation promoter, ester derivative of the carbonylatable reactant and optionally water is removed from the distillation zone and may be recycled to the carbonylation reaction; and a base process stream comprising carboxylic acid carbonylation product and optionally water is removed as a vapor or liquid from the base of the distillation zone and may be subjected to further conventional purification if necessary, for example to remove water and trace impurities such as iodides and oxidisable impurities by, for example, passing through a silver loaded ion exchange resin.

In this embodiment of the present invention the first vaporisation is preferably an adiabatic flash vaporisation and the second vaporisation is performed in a fractional distillation zone or, preferably is a partial vaporiser with addition of heat.

BRIEF DESCRIPTION OF THE DRAWINGS

The invention will now be illustrated by way of example only by reference to FIGS. 1 to 3.

DESCRIPTION OF THE PREFERRED EMBODIMENTS

Figure 1:
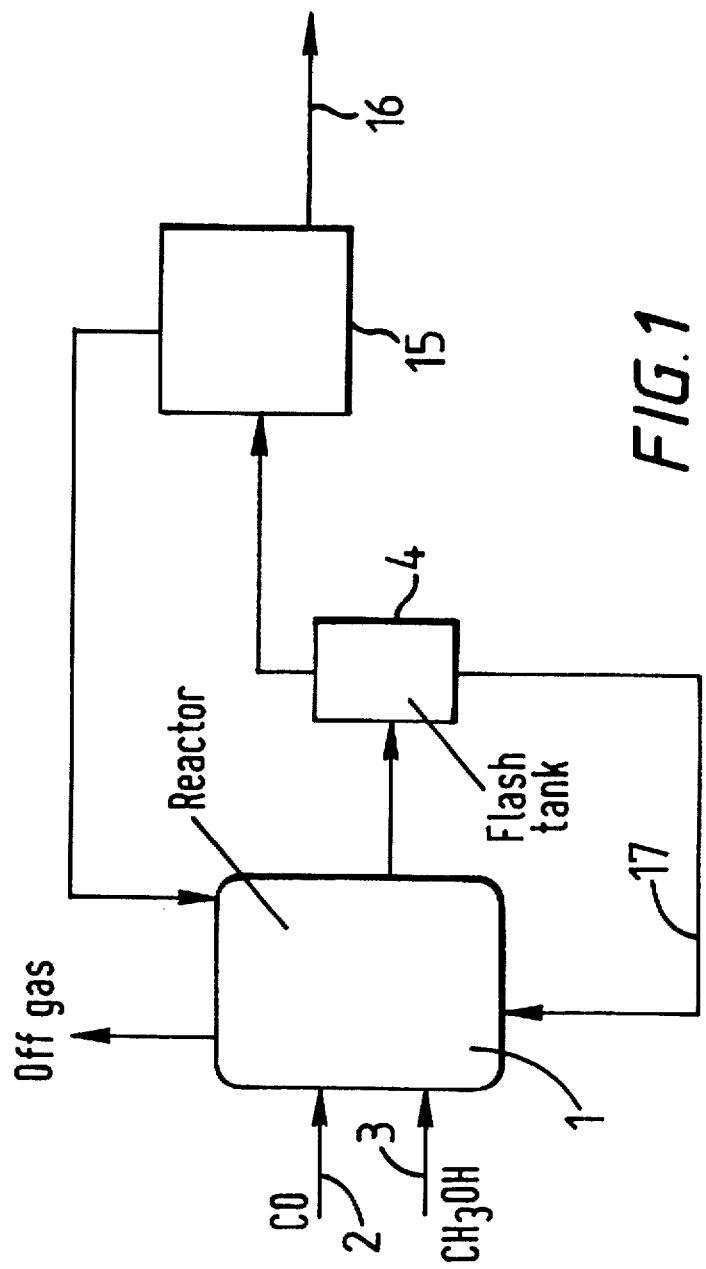
FIG. 1 represents in schematic form a flow diagram of a process according to the present invention incorporating a single flash separation stage.
Figure 2:
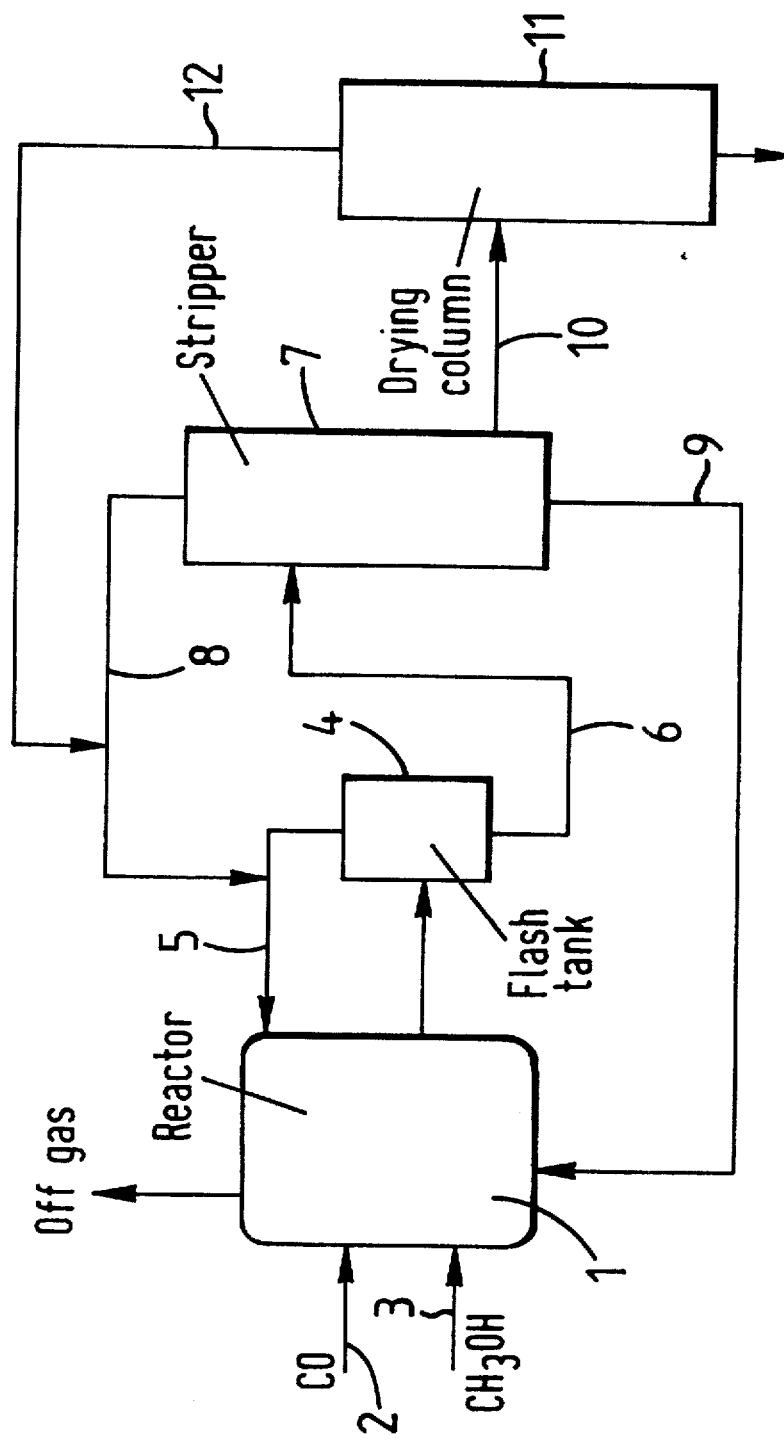
FIGS. 2 and 3 show schematic flow diagrams of two processes according to the present invention each using two separation stages.
Figure 3:
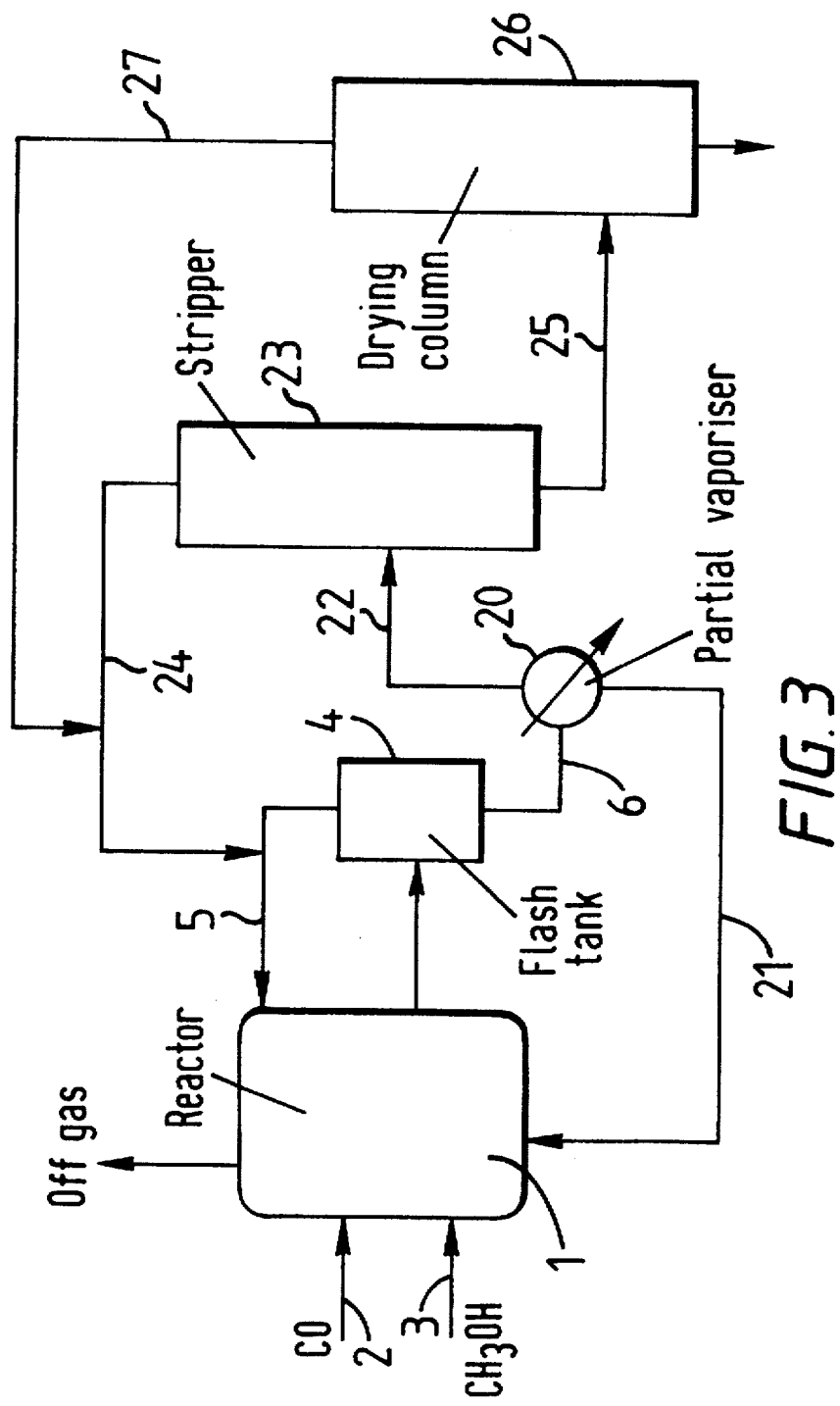

The processes in FIGS. 1 to 3 may be used for the production of acetic acid by carbonylation of methanol.

In FIGS. 1 to 3 a carbonylation reactor (1) is provided with a supply of carbon monoxide (2) and a supply of methanol (3). In use, the carbonylation reactor contains a liquid reaction composition comprising acetic acid carbonylation product, iridium carbonylation catalyst, methyl acetate derivative of methanol carbonylation reactant, methyl iodide carbonylation promoter and a finite concentration of water of at least 0.1% by weight. In use, the reactor is maintained at a pressure of 10 to 100 barg and a temperature of 100° to 250° C. In use, liquid carbonylation reaction composition is withdrawn from the reactor (1) and passed to flash zone (4) operated at a pressure below that of the reactor (for example 0 to 20 barg). This is preferably an adiabative flash zone.

In the process shown in FIG. 1 a vapor fraction comprising methyl acetate, methyl iodide, acetic acid and water is passed from the flash zone (4) to separation zone (15). This is shown schematically as a single block and may comprise one or more separation stages, for example fractional distillation zones. In this separation zone (15) acetic acid product is separated from the methyl iodide, methyl acetate and water which are recycled separately or together in one or more process streams back to the carbonylation reactor (1). The acetic acid product taken from the separation zone along line (16) may be further purified by conventional processes. In the process shown in FIG. 1 a liquid fraction comprising acetic acid, at least 0.5% by weight water and involatile iridium carbonylation catalyst is passed from the flash zone (4) and recycled along line (17) to the reactor (1).

In the embodiments shown in FIGS. 2 and 3 the flash zone (4) is operated as a preliminary separation zone to separate some of the methyl acetate and methyl iodide from the removed liquid carbonylation reaction composition. Thus, in FIGS. 2 and 3 in flash zone (4) a first vapor fraction comprising a significant amount of the methyl acetate and methyl iodide from the carbonylation reaction composition is recycled from the flash zone (4) to the reactor along line (5). A first liquid fraction comprising the remainder of the methyl acetate and methyl iodide, the iridium carbonylation catalyst and at least 0.5% by weight water is passed from the flash zone (4) along line (6).

In the embodiment shown in FIG. 2, the first liquid fraction is passed to a stripper distillation zone (7). From the top of the distillation zone (7) a process stream comprising methyl acetate and methyl iodide is taken along line (8) and recycled directly or indirectly back to the carbonylation reactor. A crude acetic acid carbonylation product is taken from the distillation zone (7) as a vapor or liquid at a point above the base of the distillation zone and passed along line (10) to a distillation zone (11). In distillation zone (11) water is removed as a head product and recycled to the reactor along line (12) and acetic acid product is taken as a base product. A second liquid fraction comprising iridium carbonylation catalyst and at least 0.5% by weight water is taken from the base of the distillation zone (7) and recycled to the reactor along line (9).

In the embodiment shown in FIG. 3, the first liquid fraction is passed to a partial vaporiser (20) in which part of the fraction is vaporised by the addition of heat to form the second vapor and liquid fractions. The second liquid fraction comprising iridium carbonylation catalyst and at least 0.5% by weight water is recycled to the reactor along line (21). The second vapor fraction comprising methyl acetate, methyl iodide, water and acetic acid is passed along line (22) to distillation zone (23). The methyl iodide and methyl acetate are taken from the distillation zone (23) as a heads product and are recycled to the reactor along line (24). A base product from the distillation zone (23) comprising acetic acid and water is taken along line (25) and passed to a distillation zone (26) from which acetic acid is recovered as a base product and water is taken as a head product and recycled along line (27) to the reactor. In the embodiment shown in FIGS. 2 and 3 the recovered acetic acid may be further purified by conventional means (not shown) to remove for example iodide and oxidisable impurities.

The invention will now be further illustrated by reference to the following examples.

A stock solution of iridium carbonylation catalyst was prepared by charging the following components to a 100 ml Hastelloy B2 (trade mark) batch autoclave fitted with a Dispersimax (trade mark) stirrer:

$IrCl_3.4H_2O$ 1.5 g methyl iodide 2.5 g water 0.75 g acetic acid balance to 50 g The autoclave was pressurised with carbon monoxide to 45 barg and then heated to 195° C. with stirring for 2 hours. After cooling to room temperature and depressurising, the stock solution was analysed by Inductively Coupled Plasma spectroscopy (ICP) for iridium content (typically about 7500 ppm). High pressure infrared analysis of similarly prepared solutions had previously indicated that they contain the species $[Ir(CO)_2I_4]^-$. This stock carbonylation catalyst solution was used in subsequent experiments.

Catalyst Stability Test 1

In a first stability test, stock carbonylation catalyst solution prepared as hereinbeforedescribed and containing about 9300 ppm iridium (8.57 g), methyl iodide (0.01 g), methyl acetate (0.73 g) and water (0.61 g) were charged to a Fischer-Porter tube, purged with carbon monoxide sealed and then heated to 100° C. with stirring for 15 minutes under autogenous pressure. This simulated the conditions which would be expected to prevail during the recovery of carbonylation product from a carbonylation composition in the second of a two-stage vaporisation according to the process of the present invention. At the end of the heating period the contents of the Fischer-Porter tube were cooled and analysed for iridium content by ICP. The Fisher-Porter tube was then reassembled and the test continued using the same solution maintained at 100° C. for 2 hours, before, repeating the analysis. The results are shown in Table 2 below.

TABLE 2

| Test No. | Test Duration (minutes) | Initial iridium concentration (ppm) | Final iridium concentration (ppm) | iridium remaining in solution (%) |
| --- | --- | --- | --- | --- |
| 1 | 15 | 9327 | 8986 | 96 |
|  | 120 | 9120 | 8854 | 97 |

Catalyst Stability Test 2

In a second stability test, stock carbonylation catalyst solution prepared as hereinbeforedescribed and containing about 9300 ppm iridium (8.51 g), methyl iodide (0.02 g), methyl acetate (0.84 g) and water (0.48 g) were charged to a Fischer-Porter tube, purged with carbon monoxide and then pressurised to 1 barg with carbon monoxide before being heated to 130° C. with stirring for 15 minutes. The pressure in the Fischer-Porter tube when at temperature was about 2.4 barg. This simulated the conditions which would be expected to prevail during the recovery of carbonylation product from a carbonylation composition in the second of a two stage vaporisation according to the process of the present invention. At the end of the heating period, the contents of the Fischer-Porter tube were cooled and analysed for iridium content by ICP. The Fischer-Porter tube was then reassembled and the test continued using the same solution maintained at 130° C. for 2 hours, before, repeating the analysis. The results are set out in the Table 3 below:

Catalyst Stability Test 3

Test 2 was repeated using a fresh charge of reagents in which the iridium catalyst stock solution contained about 17000 ppm iridium and had been prepared by removing about 50% of the acetic acid under vacuum from stock solution prepared as hereinbeforedescribed. The results are set out in Table 3 below:

TABLE 3

| Test No. | Test Duration (minutes) | Initial Iridium concentration (ppm) | Final Iridium concentration (ppm) | Iridium remaining in solution (%) |
|---|---|---|---|---|
| 2 | 15 | 9286 | 9538 | 100 |
|   | 120 | 9126 | 8976 | 94 |
| 3 | 15 | 17283 | 18097 | 96 |
|   | 120 | 18316 | 18035 | 100 |

The results of tests 1 to 3 show that the iridium catalyst is stable in the presence of at least 0.5% water.

Catalyst Stabilily Test 4

Test 2 was repeated but without addition of methyl iodide to the Fischer Porter tube. The results are shown in Table 4 below.

Catalyst Stability Test 5

Test 2 was repeated but without addition of methyl acetate to the Fischer Porter tube. The results are shown in Table 4 below.

Comparative Example A

Test 2 was repeated using the following initial charge:
catalyst stock solution 9.094 g
methyl acetate 0.873 g
methyl iodide 0.024 g.

The water content of the mixture charged was measured by the Karl Fischer method to be only 0.33% by weight. The analysis of iridium concentration after 120 minutes shown in Table 5 below shows that when the water content is less than 0.5% by weight the iridium catalyst does not remain in solution.

TABLE 4

| Test No. | Test Duration (minutes) | Initial Iridium concentration (ppm) | Final Iridium concentration (ppm) | Iridium remaining in solution (%) |
|---|---|---|---|---|
| 4 | 120 | 9839 | 9572 | 97 |
| 5 | 120 | 9851 | 9895 | 100 |

TABLE 5

| Test No. | Test Duration (minutes) | Initial Iridium concentration (ppm) | Final Iridium concentration (ppm) | Iridium remaining in solution (%) |
|---|---|---|---|---|
| A | 120 | 9342 | 8263 | 88 |

We claim:

1. A process for the recovery of a fraction comprising a carboxylic acid carbonylation product of an alcohol, ester, hydrocarbyl halide and/or hydrocarbyl ether carbonylatable reactant from a liquid carbonylation reaction composition comprising carboxylic acid carbonylation product, free or combined iridium carbonylation catalyst and ester derivative of the carbonylatable reactant which process comprises: (a) subjecting the liquid carbonylation reaction composition to a vaporization in a first vaporization zone to produce, with or without the addition of heat, a first vapor fraction comprising at least a portion of the ester derivative in the liquid carbonylation reaction composition and a first liquid fraction comprising the remainder of the ester derivative in the liquid carbonylation reaction composition, at least a portion of the carboxylic acid product and the iridium carbonylation catalyst, and maintaining a concentration of water of at least 0.5% by weight to 50% by weight for the purpose of stabilizing the iridium catalyst in the first liquid fraction; and (b) passing the first liquid fraction to a second vaporization zone wherein the first liquid fraction is subjected to a vaporization, with or without the addition of heat, to produce a second vapor fraction comprising carboxylic acid carbonylation product and a second liquid fraction comprising iridium carbonylation catalyst and maintaining in the second liquid fraction a concentration of water of at least 0.5% by weight for the purpose of stabilizing the catalyst; and (c) recycling said stabilized iridium carbonylation catalyst.

2. A process as claimed in claim 1 which further comprises recovering carboxylic acid carbonylation product from said second vapor fraction by fractional distillation.

3. A process for the recovery of an iridium carbonylation catalyst from a liquid reaction composition obtained from an iridium-catalysed carbonylation reaction of a carbonylatable reactant, which liquid composition consists essentially of carbonylation product, carbon monoxide, an alkyl halide carbonylation promoter, water, and iridium carbonylation catalyst and at least one component selected from the group consisting of said carbonylatable reactant and an ester derivative of said carbonylatable reactant, which process comprises: (a) subjecting said liquid composition to at least one vaporization, with or without the addition of heat, to product at least one vapor fraction comprising carbonylation product and at least one liquid fraction comprising iridium carbonylation catalyst and water; (b) separating the liquid and vapor fractions while maintaining in said at least one liquid fraction a concentration of water of at least 0.5% by weight to 50% by weight for the purpose of stabilizing said catalyst; and (c) recycling said stabilized catalyst to said carbonylation reaction.

* * * * *